United States Patent

Metz et al.

[11] Patent Number: 5,770,780
[45] Date of Patent: Jun. 23, 1998

[54] PROCESS FOR PREPARING ALKYL HALIDES

[75] Inventors: Josef Metz, Marl; Clemens Osterholt, Dorsten, both of Germany

[73] Assignee: Huels Aktiengesellschaft, Marl, Germany

[21] Appl. No.: 799,068

[22] Filed: Feb. 10, 1997

[30] Foreign Application Priority Data

Feb. 8, 1996 [DE] Germany ................. 196 04 566.5

[51] Int. Cl.$^6$ .................................................. C07C 17/08
[52] U.S. Cl. ............................................................ 570/248
[58] Field of Search ................... 570/246, 247, 570/248

[56] References Cited

PUBLICATIONS

CA:88:6374 Abst of Syunthetic Methods & Reactions PC–Promoted Halogenation of Alhenes with Hydrohali Acids/$H_2O_2$—1977.
Chemistry & Physics Handbook 1958, pp. 890–891.
Research Disclosure, Nr. 355, Nov. 1993, "Hydrohalogenation of Cyclopentene", p. 754.

*Primary Examiner*—Alan L. Rotman
*Assistant Examiner*—Jean F. Vollano
*Attorney, Agent, or Firm*—Oblon, Spivak, McClelland, Maier & Neustadt, P.C.

[57] ABSTRACT

In the preparation of alkyl halides from cycloaliphatic olefins and hydrohalic acids, the reaction is carried out at a temperature below the boiling point of the olefin without the addition of catalyst and without a solvent. At a high olefin conversion rate, alkyl halides are obtained with high selectivity and with very good color quality.

25 Claims, 1 Drawing Sheet

PROCESS FOR PREPARING ALKYL HALIDES

BACKGROUND OF THE INVENTION

1. Field of the Invention:

The invention relates to a novel process for preparing alkyl halides from cycloaliphatic olefins having 5–16 carbon atoms and concentrated hydrohalic acid.

2. Discussion of the Background:

Alkyl halides serve as solvents. In addition, they are used for Friedel-Crafts alkylations, for preparing organometallic compounds and for the synthesis of crop protection agents and pharmaceutical products.

In the preparation of alkyl halides, one generally starts from alcohols or olefins. Tetrahedron 23, 2051 (1967), discloses the preparation of cyclooctyl chloride from cyclooctene and hydrochloric acid with the presence of zinc chloride, in benzene as a solvent. According to JP 89/166 393, $AlCl_3$, $FeCl_3$, $NiCl_2$ or CuCl can used as a catalyst for preparing cycloaliphatic alkyl chlorides, with methylene chloride, chloroform or carbon tetrachloride as a solvent. These processes are laborious or complex, since the solvent must be separated off and catalysts must be worked up.

SUMMARY OF THE INVENTION

An object of the present invention is to provide a simplified process for preparing alkyl halides from cycloaliphatic olefins.

This object is achieved by a process comprising, reacting a cycloaliphatic olefin and a haloacid at a temperature below the boiling point of the olefin, without the addition of a catalyst and without a solvent.

DETAILED DESCRIPTION OF THE INVENTION

Figure 1:
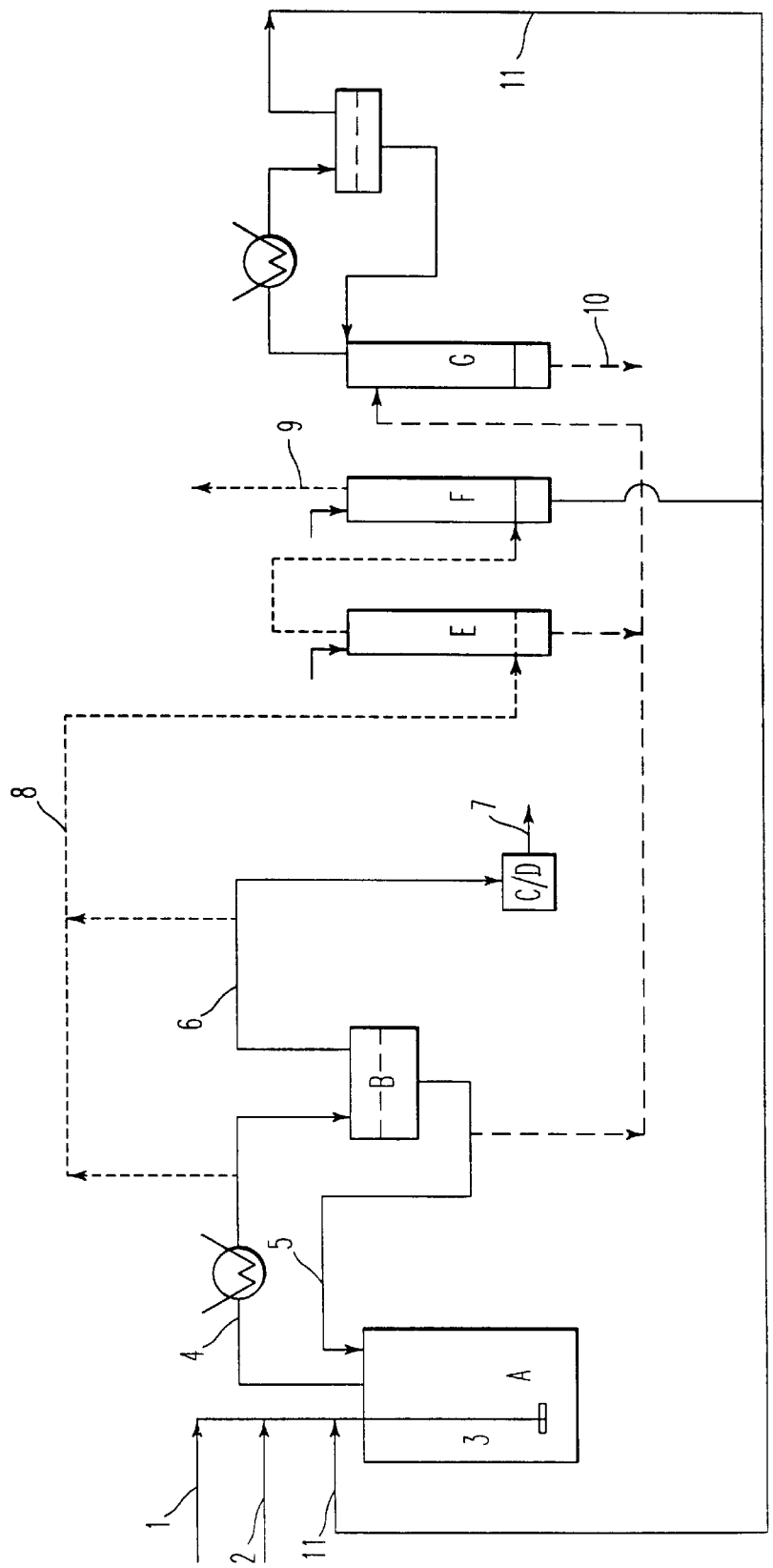
FIG. 1 shows an apparatus and steps described in the Examples.

Suitable cycloaliphatic olefins have 5–16 carbon atoms, preferably 5–10 carbon atoms. Examples include cyclopentene, cyclohexene, cycloheptene, cyclooctene, 1-methyl-1-cyclopentene, 1,2-dimethyl-1-cyclohexene, 1,4-dimethyl-1-cyclooctene and 1,4-cyclooctadiene.

Hydrohalic acids which are suitable are hydrochloric acid, hydrobromic acid and hydroiodic acid. Concentrated hydrohalic acids in the context of this invention are acids of at least 20% strength. Preferably, 20–45% strength hydrochloric acid is used. All strengths of acids are weight percentages in water.

Preferably cyclic alkyl chlorides are prepared.

The reaction temperature depends on the boiling point of the olefin used. In the process of the present invention, the reaction temperature is preferably in the range from 0°–110° C. In addition to a batch mode, a continuous process procedure is also possible.

A general advantage of the process of the present invention is that the reaction can be carried out at atmospheric pressure. Surprisingly, alkyl halides are obtained by this process at high olefin conversion rates, in high purity and with selectivity, in addition to very good color. Alkaline scrubbing is not required. At most only very simple purification by distillation is required for further color improvement.

In the context of the present invention, a solvent is an organic solvent, present at more than 10%, preferably more than 5%, more preferably 1%, by weight, which does not react or form during the process, and is not a standard additive in one of the reactants, or impurity. For example, water present in the concentrated hydrohalic acid, or a small amount of an alkane in the olefin, are not solvents.

Preferably, the reaction is carried out with at most 10%, more preferably at most 5%, even more preferably at most 1%, by weight, of an organic solvent, including benzene, methylene chloride, chloroform or carbon tetrachloride.

Having generally described this invention, a further understanding can be obtained by reference to certain specific examples which are provided herein for purposes of illustration only and are not intended to be limiting unless otherwise specified.

EXAMPLES

Example 1

Preparation of cyclopentyl chloride (FIG. 1)

100 g of concentrated hydrochloric acid (approximately 36% strength) are introduced into an $N_2$-blanketed glass reactor (A), set to 10° C. 340 g of cyclopentene, technical grade (contents by gas chromatography (GC): 96.7%, 3.2% of cyclopentane), are then added.

At the above-mentioned reactor temperature, the reaction is carried out by introducing hydrogen chloride (3) in the course of approximately 23 hours up to a residual cyclopentene content of <1%.

The exhaust gas, predominantly hydrogen chloride and nitrogen, containing a small amount of cyclopentene and cyclopentyl chloride, is fed via a collecting line (8), for the absorption of HCl, to an $H_2O$ counter-current scrubber (E) and then, for the absorption of cyclopentyl chloride, to a cyclopentanol counter-current scrubber (F). The exhaust gas (9) thus cleaned is fed for disposal to an exhaust gas incineration unit. The cyclopentyl chloride-enriched cyclopentanol from the counter-current scrubber (F) is fed into the reactor (A).

The process waste waters are adjusted to a pH of <7 and fed to the stripping column (G) for removal of organic constituents. The upper organic phase of the azeotrope arising there (predominantly cycloalkyl chlorides, cycloolefins and aqueous hydrochloric acid) is recycled to the reactor (A) and the lower aqueous azeotropic phase is passed to the lower section of the stripping column. The bottom phase (10) freed of organic contents is fed to a waste water treatment plant.

After the end of the reaction, the phases are separated. The lower aqueous phase is used for the following batch, or at the end of the batch is fed to the stripping column (G). The upper organic cycloalkyl chloride phase is subjected to vacuum drying and taken off for further workup [alkaline drying (C/D) and, if appropriate, purification by distillation]. The distillate arising in the vacuum drying is added to the following batch.

Product composition of a distilled material is shown in the table.

TABLE

| | |
|---|---|
| Cyclopentane | : < 0.05% |
| Cyclopentene | : < 0.05% |
| Dicyclopentyl ether | : ≦ 0.001% |
| Cyclopentyl chloride | : > 99.5% |
| APHA color | : < 10% |
| Yield | : 93% of theoretical prediction |

Example 2

Preparation of Cyclohexyl Chloride (FIG. 1)

200 g of concentrated hydrochloric acid (approximately 36% strength) and 600 g of cyclohexene (>99.5% pure) are charged into the reactor (A) under $N_2$ blanketing. The reaction is carried out similarly to Example 1 at a reaction temperature of 40° C. in approximately 20 hours.

The counter-current scrubber (F) is operated with cyclohexanol. After phase separation and vacuum drying have been performed, a cyclohexyl chloride >99% pure by GC analysis is obtained having an APHA color index of approximately 20–30.

By a single short-path flash distillation, the APHA color index can be improved to ≦10. The yield is >95% of theoretical prediction.

Example 3
Preparation of Cyclooctyl Chloride (FIG. 1)

100 g of concentrated hydrochloric acid (approximately 36% strength) and 411 g of cyclooctene (96.4% pure, 3.6% cyclooctane) are charged into the reactor (A) under $N_2$, blanketing and the reaction is carried out similarly to Example 1 at a reactor temperature of 40° C. in approximately 95 hours.

The counter-current scrubber (F) is operated with cyclooctanol. After phase separation and vacuum drying have been performed, 98.9% pure cyclooctyl chloride, according to the $^{13}$C-NMR spectrum, having an APHA color index of approximately 50 is obtained.

By single short-path flash distillation, the APHA color index is improved to ≦10. The yield is >95% of theoretical prediction.

Obviously, additional modifications and variations of the present invention are possible in light of the above teachings. It is therefore to be understood that within the scope of the appended claims, the invention may be practiced otherwise than as specifically described herein.

The priority document of the present application, German patent application 196 04 566.5, filed Feb. 8, 1996, is hereby incorporated by reference.

What is claimed as new and desired to be secured by letters patent of the United States is:

1. A process for the preparation of cycloalkyl halides, consisting essentially of:
   reacting an olefin and concentrated hydrohalic acid, without the addition of a catalyst and without addition of a solvent;
   wherein said reacting is carried out at a temperature below the boiling point of said olefin, and said olefin is a cycloaliphatic olefin having 5–16 carbon atoms.

2. The process of claim 1, wherein said olefin has 5–10 carbon atoms.

3. The process of claim 1, wherein said temperature is 0°–110° C.

4. The process of claim 1, wherein said alkyl halide is an alkyl chloride.

5. The process of claim 1, wherein said olefin is selected from the group consisting of cyclopentene, cyclohexene, cycloheptene, cyclooctene, 1-methyl-1-cyclopentene, 1,2-dimethyl-1-cyclohexene, 1,4-dimethyl-1-cyclooctene and 1,4-cyclooctadiene.

6. The process of claim 1, wherein said alkyl halide is prepared in a yield of at least 93%, based on said olefin.

7. A process, comprising:
   adding a hydrogen halide to a liquid comprising concentrated hydrohalic acid and an olefin, thereby forming an cycloalkyl halide;
   wherein said liquid comprises at most 10% by weight of an organic solvent,
   said liquid is at a temperature below the boiling point of said olefin, and
   said olefin is a cycloaliphatic olefin.

8. The process of claim 7, wherein said liquid comprises at most 5% by weight of an organic solvent.

9. The process of claim 7, wherein said liquid comprises at most 1% by weight of an organic solvent.

10. The process of claim 7, wherein said concentrated hydrohalic acid is hydrochloric acid.

11. The process of claim 7, wherein said olefin has 5–16 carbon atoms.

12. The process of claim 11, wherein said liquid comprises at most 5% by weight of an organic solvent.

13. The process of claim 12, wherein said olefin has 5–10 carbon atoms.

14. The process of claim 12, wherein said temperature is 0°–110° C.

15. The process of claim 12, wherein said alkyl halide is an alkyl chloride.

16. The process of claim 12, wherein said adding is carried out continuously for at least one hour.

17. The process of claim 12, wherein said olefin is selected from the group consisting of cyclopentene, cyclohexene, cycloheptene, cyclooctene, 1-methyl-1-cyclopentene, 1,2-dimethyl-1-cyclohexene, 1,4-dimethyl-1-cyclooctene and 1,4-cyclooctadiene.

18. The process of claim 12, wherein said alkyl halide is prepared in a yield of at least 93%, based on said olefin.

19. The process of claim 18, wherein said alkyl halide is prepared in a yield of at least 95%, based on said olefin.

20. A process, comprising:
   adding a hydrogen halide to a first liquid comprising concentrated hydrohalic acid and an olefin, thereby forming an alkyl halide; followed by
   separating said liquid into (i) a first aqueous phase, and (ii) a second organic phase; and, followed by
   adding said hydrogen halide to a second liquid comprising said olefin and said first aqueous phase, thereby forming said cycloalkyl halide;
   wherein said first liquid comprises at most 10% by weight of an organic solvent,
   said liquid is at a temperature below the boiling point of said olefin, and
   said olefin is a cycloaliphatic olefin having 5–6 carbon atoms.

21. The process of claim 1, wherein said process is carried out at atmospheric pressure.

22. The process of claim 7, wherein said process is carried out at atmospheric pressure.

23. The process of claim 7, wherein said process is carried out without a catalyst.

24. The process of claim 20, wherein said process is carried out at atmospheric pressure.

25. The process of claim 20, wherein said process is carried out without a catalyst.

* * * * *